United States Patent [19]

Suzuki et al.

[11] Patent Number: 4,931,289
[45] Date of Patent: Jun. 5, 1990

[54] ORAL PHOSPHATE ION ADSORBENT

[75] Inventors: Takeshi Suzuki, Tokushima; Mineaki Kabayama, Naruto, both of Japan

[73] Assignee: Tomita Pharmaceutical Co., Ltd., Tokushima, Japan

[21] Appl. No.: 271,329

[22] Filed: Nov. 15, 1988

[30] Foreign Application Priority Data

Nov. 16, 1987 [JP] Japan .................................. 62-290215

[51] Int. Cl.$^5$ ............................................. A61K 33/08
[52] U.S. Cl. ...................................................... 424/690
[58] Field of Search ......................................... 424/690

[56] References Cited

U.S. PATENT DOCUMENTS 4,514,511  4/1985  Jacques et al. ......................... 502/8

Primary Examiner—Douglas W. Robinson
Assistant Examiner—Raymond J. Henley, III
Attorney, Agent, or Firm—Larson and Taylor

[57] ABSTRACT

An oral phosphate ion-adsorbing agent containing as an effective component a boehmite-type aluminum hydroxide which is represented by the formula $$AlO(OH) \cdot nH_2O$$

wherein $0 \leq n < 1$ and which is about 0.2 to about 1.0 meq/g in the amount of active OH group present on the surface thereof and at least about 200 m$^2$/g in the BET specific surface area.

8 Claims, 7 Drawing Sheets

ORAL PHOSPHATE ION ADSORBENT

BACKGROUND OF THE INVENTION

This invention relates to an oral adsorbent for adsorbing phosphate ions.

A phosphate ion adsorbent adsorbs or binds to the phosphoric acid delivered to intestines by the food containing the same, preventing the absorption of the acid in the body. With this activity, the phosphate ion adsorbent is orally administered chiefly to patients of hyperphosphatemia, renal insufficiency or the like. While a dried aluminum hydroxide gel has been conventionally used as an oral phosphate ion adsorbent, a long-term use of dried aluminum hydroxide gel results in the decomposition thereof due to the alkaline liquid in intestines, the gastric acid or the like, accumulating a large amount of Al ions produced in the body which cause dialysis encephalopathy, aluminum poisoning or the like.

In view of this problem, a calcium carbonate agent is currently used in place of dried aluminum hydroxide gel. However, this agent is also prone to decomposition owing to the gastric acid or the like which leads to production of a large amount of Ca ions liable to induce hypercalcemia. Further the agent is lower by about 20 to about 25% in the capacity of adsorbing phosphate ions than dried aluminum hydroxide gel.

Other various adsorbents are available but have problems in terms of the safety of human body and insufficient phosphate ion-adsorbing capacity.

SUMMARY OF THE INVENTION

It is an object of the present invention to provide an oral phosphate ion-adsorbing agent having an outstanding phosphate ion-adsorbing capacity.

It is another object of the invention to provide an oral phosphate ion-adsorbing agent which is stable to the actions of the gastric acid as well as the alkaline liquid in intestines and which does not release Al ions.

It is a further object of the invention to provide an oral phosphate ion-adsorbing agent which causes no disease such as dialysis encephalopathy, aluminum poisoning or the like by a long-term administration thereof.

Other objects and features of the present invention will become apparent from the following description.

DETAILED DESCRIPTION OF THE INVENTION

Figure 1:
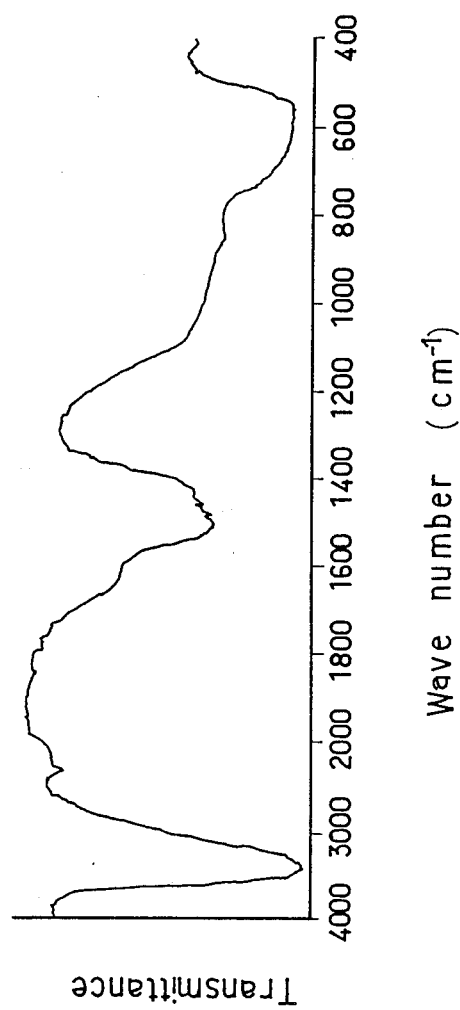

The present invention provides an oral phosphate ion-adsorbing agent containing as an effective component a boehmite-type aluminum hydroxide which is represented by the formula $$AlO(OH) \cdot nH_2O \quad (1)$$

wherein $0 \leq n < 1$ and which is about 0.2 to about 1.0 meq/g in the amount of active OH group present on the surface thereof and at least about 200 m²/g in the BET specific surface area, and an adsorbing method characterized by an oral administration of the agent.

The term "active OH group" used herein refers to the OH group having a phosphate ion-adsorbing capacity.

Our research revealed: (1) the hydrothermal treatment of amorphous aluminum hydroxide at a specific temperature gives a boehmite-type aluminum hydroxide having a significantly large amount of active OH group present on the surface thereof and a pronouncedly great BET specific surface area, (2) the boehmite-type aluminum hydroxide has an outstanding phosphate ion-adsorbing capacity and (3) the boehmite-type aluminum hydroxide is highly stable to the actions of the gastric acid as well as the alkaline liquid in intestines so that a long-term use thereof brings about little accumulation of Al ions in the body.

Preferred classes of the boehmite-type aluminum hydroxide of the formula (1) (hereinafter referred to as "boehmite (1)") include those wherein $0.3 \leq n \leq 0.6$. The boehmite (1) wherein n is in this range has both a large amount of active OH group and a great BET specific surface area.

The boehmite (1) can be prepared by the hydrothermal treatment of amorphous aluminum hydroxide, followed by drying.

The hydrothermal treatment is carried out by heating an aqueous dispersion of amorphous aluminum hydroxide (aluminum hydroxide gel) to about 60° to about 100° C., preferably about 80° to about 100° C. This treatment may be effected with stirring. The heating temperature exceeding 100° C. results in a boehmite having a reduced phosphate ion-adsorbing capacity, whereas the heating temperature below 60° C. markedly retards conversion into boehmite and fails to produce a boehmite with the desired phosphate ion-adsorbing capacity and BET specific surface area. The heating time is not specifically limited but usually ranges from about 1 to about 5 hours. The concentration of amorphous aluminum hydroxide in the aluminum hydroxide gel is not specifically limited but usually ranges from about 1 to about 10% by weight.

The drying is conducted by conventional methods, preferably using an spray drier to obtain a boehmite with a greater specific surface area.

An amorphous aluminum hydroxide useful as a starting material for the boehmite (1) can be prepared by reacting a water-soluble aluminum salt with a water-soluble alkali salt or ammonia in an aqueous medium. Useful water-soluble aluminum salts include conventional ones such as aluminum sulfate, aluminum chloride, aluminum nitrate and the like. Useful water-soluble alkali salts include conventional ones such as sodium carbonate, potassium carbonate, sodium hydrogencarbonate and the like. The process for preparing amorphous aluminum hydroxide is known and disclosed, for example, in Japanese Examined Patent Publication No. 3529/1955.

The amorphous aluminum hydroxide thus obtained has an unstable structure and a small BET specific surface area so that it is low in the physical phosphate ion-adsorbing capacity. Yet when hydrothermally treated at a specific temperature, the amorphous aluminum hydroxide is converted into the boehmite (1) having an excellent phosphate ion-adsorbing capacity and a great BET specific surface area. The hydrothermal treatment of other types of aluminum hydroxide such as gibbsite-type aluminum hydroxide (hereinafter referred to simply as "gibbsite") forms also a boehmite-type one in which, however, because of the strong Al-OH bond of gibbsite, the gibbsite structure tends to partially remain and only about 0.2 meq/g or less of active OH groups is achieved. This fact is supported by IR analysis of the boehmite produced from gibbsite in which the Al-OH bond of gibbsite is detected. The boehmite thus formed from gibbsite does not exhibit the same specific range of OH group amount or BET specific surface area as in the present invention. Consequently an adsorbent having the desired phosphate ion-adsorbing capacity can not be obtained.

The boehmite (1) produced by the hydrothermal treatment has the following characteristics:

(i) Amount of active OH group

The amount of active OH group present on the surface is about 0.2 to about 1.0 meq/g, preferably about 0.3 to about 0.9 meq/g.

The amount of active OH group is given as the neutralization equivalent obtained by a titration using a 1N hydrochloric acid. More specifically, 1 g of test compound is suspended in 100 ml of pure water and the suspension is titrated by a completely automated titrator using 1N hydrochloric acid whereupon the neutralization equivalent is measured by the change of electric potential.

(ii) Layer structure

Water, ions and the like are likely to be included in the layer. The layer has a specific surface area about 3 to 6 times as great as that of amorphous aluminum hydroxide or gibbsite, i.e. about 200 m$^2$/g or more, usually about 200 to about 400 m$^2$/g, which shows that the boehmite (1) of the invention has a remarkable phosphate ion-adsorbing capacity. (iii) Color The boehmite (1) has a white color.

The boehmite (1) having the particle size adjusted to the desired one can be used.

The phosphate ion-adsorbing agent of the present invention containing the boehmite (1) as an effective component is orally administered. The dose administered is not specifically limited and is suitably determined. The adsorbent of the invention is usually administered at a daily dose of about 3 to about 6 g per adult, and given in 3 or 4 divided doses per day. This dose corresponds to ½ to about 1/5 that of dried aluminum hydroxide gel or precipitated calcium carbonate conventionally used.

The present invention will be further clarified with reference to the following Examples and Comparison Examples in which the percentages are all by weight.

Example 1

To 14 l of water at 20° C. were added dropwise 15.9 kg of an aqueous solution of aluminum sulfate (8% Al$_2$O$_3$) and 15.7 kg of a 30% aqueous solution of sodium carbonate at the same time with stirring to obtain an aluminum hydroxide gel (final liquid having a pH of 6.6).

The obtained aluminum hydroxide gel was washed with water and dried, giving a powder (a) of amorphous aluminum hydroxide. Table 1 below shows properties of the powder (a).

FIG. 1 shows the IR spectrum of the powder (a). In FIG. 1, the peak at 3000 to 3500 cm$^{-1}$ indicates the presence of active OH groups, the peak at about 1650 cm$^{-1}$ the presence of H$_2$O molecules and the peaks at 1400 cm$^{-1}$ and 850 cm$^{-1}$ the presence of carbonate ions.

The aluminum hydroxide gel obtained in the same manner as above was heated with stirring to 90° C., maintained at the same temperature for 2 hours with stirring, washed with water and dried at 60° to 80° C.,  giving a powder (b) of the boehmite of the invention. Table 1 below shows properties of the powder (b).

Figure 2:
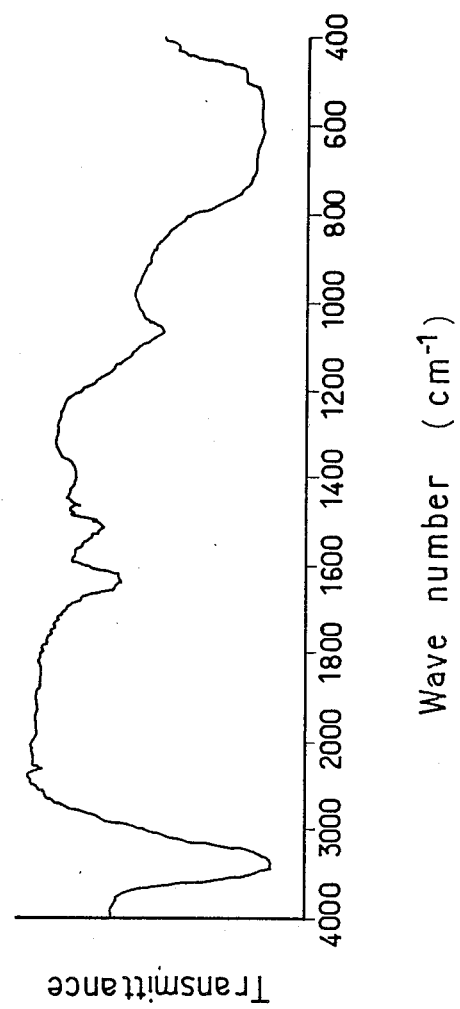

FIG. 2 indicates the IR spectrum of the powder (b). In FIG. 2, the peak at 3000 to 3500 cm$^{-1}$ shows the presence of active OH groups and the peak at about 1650 cm$^{-1}$ the presence of H$_2$O molecules. A shape slightly resembling a peak can be recognized at 1400 cm$^{-1}$ but no peak is seen at about 850 cm$^{-1}$. The carbonate ions present in the powder (a) were presumably removed with the progress of conversion to boehmite. The peak at 1060 to 1080 cm$^{-1}$ is presumed to show that peculiar to boehmite.

Comparison Example 1

To water at 26° C. were added dropwise 1880 g of an aqueous solution of aluminum sulfate (8% Al$_2$O$_3$) and 1500 g of an aqueous solution of sodium aluminate (20% Al$_2$O$_3$) at the same time with stirring, giving an aluminum hydroxide precipitate (final liquid having a pH of 10.8). The thus obtained aluminum hydroxide precipitate was washed with water and dried, giving a gibbsite-type aluminum hydroxide powder (c).

A portion of the gel was treated in the same manner as the process for producing the the powder (b) in Example 1, giving a powder (d) of boehmite-type aluminum hydroxide. Table 1 below shows properties of the powders (c) and (d).

Figure 3:
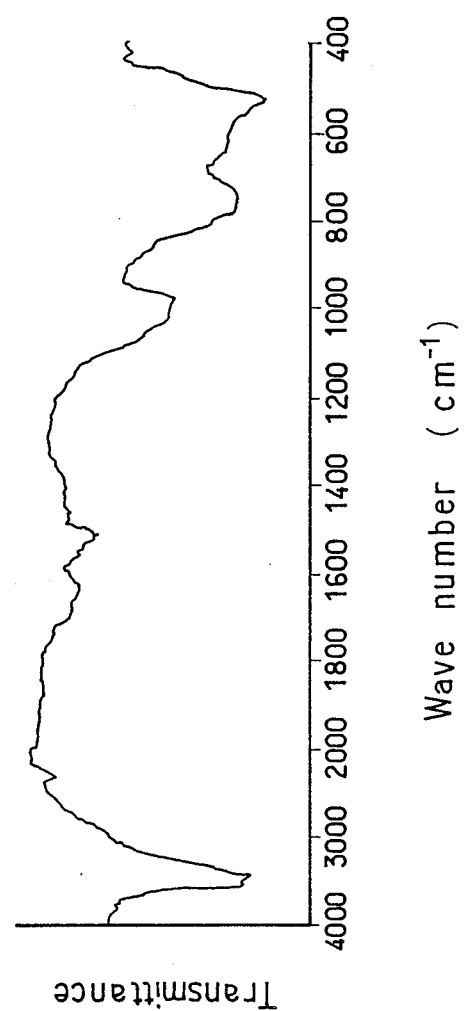
Figure 4:
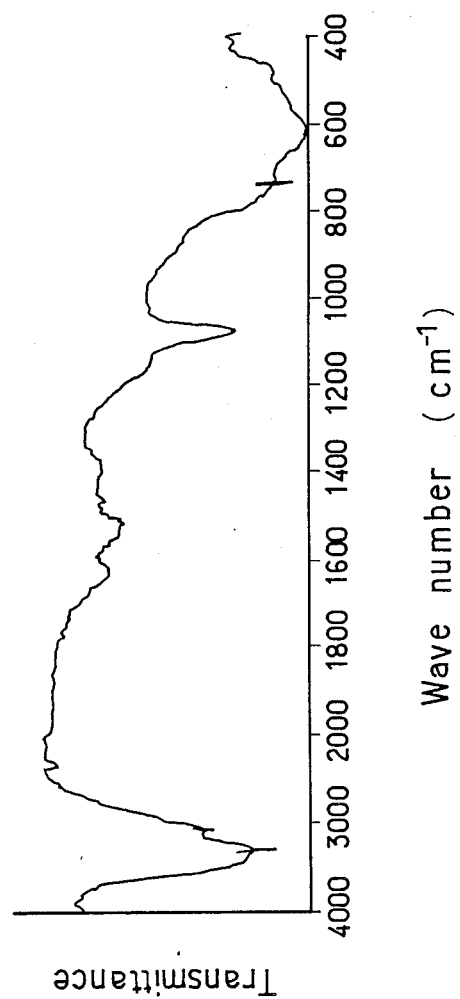

FIGS. 3 and 4 indicate the IR spectrum of the powders (c) and (d).

In FIG. 3, the peaks at 3500 to 3520 cm$^{-1}$ and 3400 to 3450 cm$^{-1}$ show the presence of bound OH groups peculiar to gibbsite. Yet the presence of active OH groups was not confirmed. The peak at about 1650 cm$^{-1}$ indicates the presence of H$_2$O molecules. The peaks at 1024 cm$^{-1}$ and 975 cm$^{-1}$ show those peculiar to gibbsite. The peak at about 750 cm$^{-1}$ is indicative of the strong bond of Al-OH group.

In FIG. 4, the peaks at about 3080 cm$^{-1}$ and about 3250 cm$^{-1}$ show those peculiar to boehmite suggestive of conversion from gibbsite. No active OH group was recognized. The peak at about 1650 cm$^{-1}$ shows the existence of H$_2$O molecules and the peak at about 1080 cm$^{-1}$ that peculiar to boehmite. The peak at 750 cm$^{-1}$ indicates the remaining Al-OH bond of gibbsite.

Test for phosphate ion-adsorbing capacity

A 0.5 g portion of the specimen was added to 100 ml of an aqueous solution of 0.01% disodium phosphate and the mixture was stirred at 37°±2° C. for 1 hour. After cooling, the solids were filtered off by a glass filter. To 10 ml of the filtrate thus obtained were added 2 ml of 10% sulfuric acid and 1 ml of a solution of ammonium molybdate (5 w/v). The mixture was stirred for 5 minutes. The absorbance (=equilibrium concentration (mgP/g)) at 389 nm was measured by a spectrophotometer. The same procedure was conducted in respect of a blank. The concentration of blank was obtained on the basis of the absorbance measured according to the specified calibration line. The percentage of adsorption (%) was calculated by the following equation. Percentage of adsorption (%)=

$$\frac{\text{Blank concentration} - \text{Equilibrium concentration}}{\text{Blank concentration}} \times 100$$

TABLE 1

|  | Example 1 | | Comparison Example 1 | |
| --- | --- | --- | --- | --- |
|  | Powder (a) (before heating) | Powder (b) (after heating) | Powder (c) (before heating) | Powder (d) (after heating) |
| $Al_2O_3$ (%) | 53.70 | 62.11 | 63.55 | 69.49 |
| Decreased amount on drying (%) | 13.65 | 14.05 | 5.02 | 10.04 |
| Decreased amount on heating (%) | 46.30 | 37.89 | 36.45 | 30.51 |
| Value of n in the formula: $AlO(OH) \cdot nH_2O$ | 0.87 | 0.56 | 0.87 | 0.30 |
| Specific surface area (m²/g) | 78.9 | 329.7 | 70.1 | 237.0 |
| Amount of active OH group (meq/g) | 0.454 | 0.762 | 0.042 | 0.173 |
| Percentage of absorption of phosphate ions (%) | 78.9 | 100.0 | 28.6 | 30.6 |
| Crystaline structure (obtained by X-ray diffraction) | Amorphous | Boehmite | Gibbsite | Boehmite |

EXPERIMENT EXAMPLE 1

Figure 5:
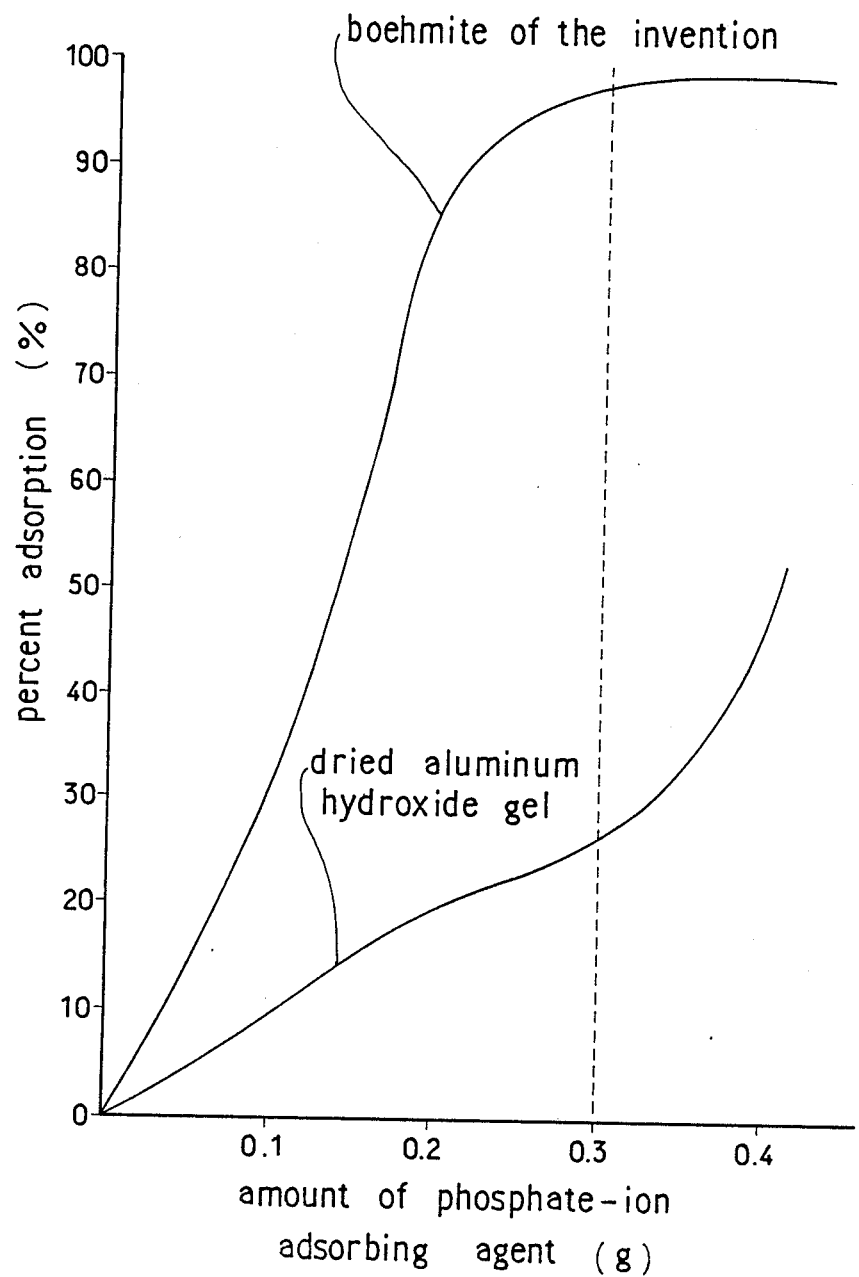

Using varied amounts of the boehmite of the invention prepared in Example 1 and dried aluminum hydroxide gel (Japanese Pharmacopoeia), the percent adsorption varied with respective amounts thereof was determined. The same procedure as in the phosphate-ion adsorbing test described above was repeated with the exception of using the adsorbing agent in amounts varied from 0.1 to 0.4 g. FIG. 5 shows the results.

FIG. 5 reveals that the boehmite of the invention exhibits much greater phosphate-ion adsorbing capacity than the dried aluminum hydroxide gel and that the boehmite of the invention used in about ⅓ the amount of dried aluminum hydroxide gel has practically the same level of phosphate-ion adsorbing capacity as the gel.

EXPERIMENT EXAMPEL 2

Figure 6:
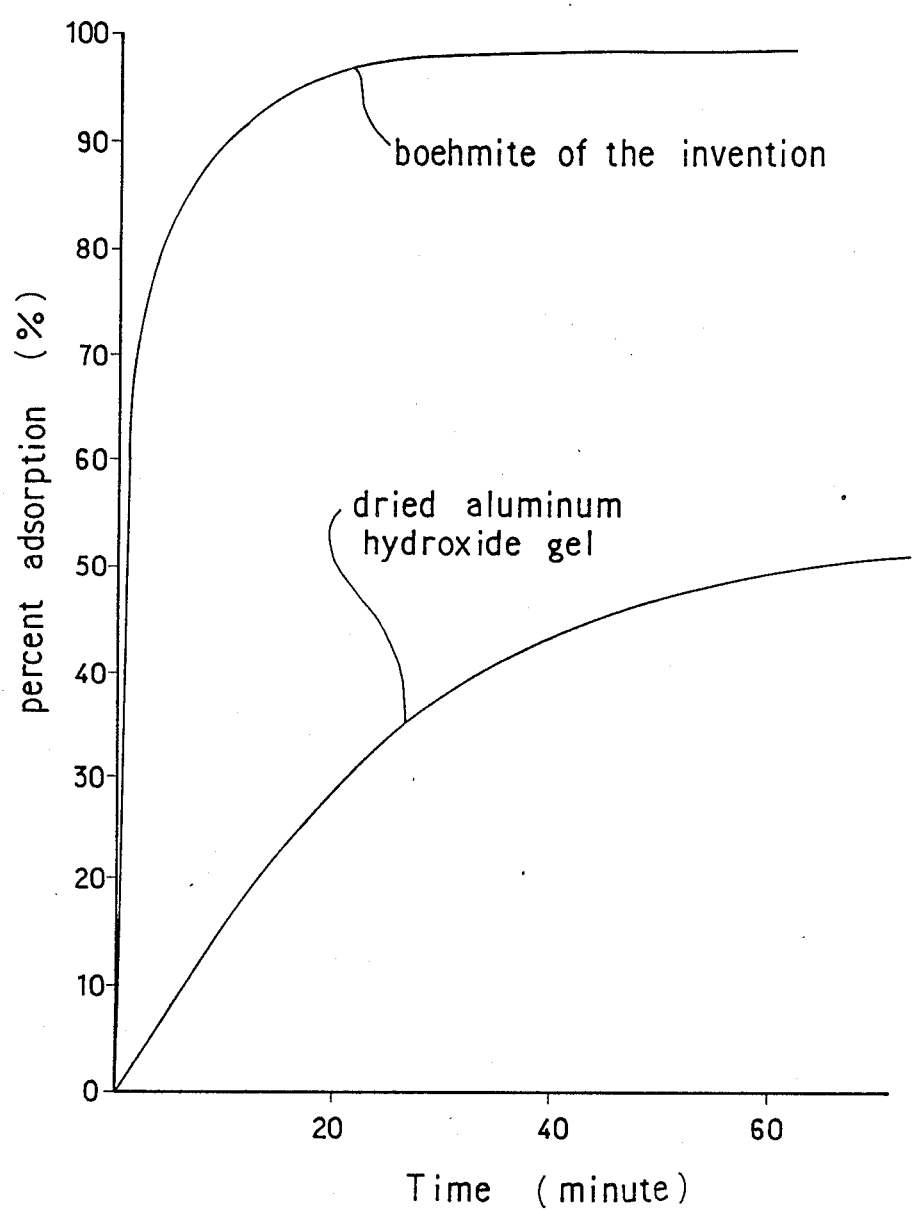

Using the boehmite of the invention prepared in Example 1 and dried aluminum hydroxide gel (Japanese Pharmacopoeia), their rate of adsorbing phosphate ions was determined. The test was conducted in the same manner as in the phosphate ion-adsorbing test stated above, using 0.40 g of the specimen and stirring for 20, 40 and 60 minutes, respectively. FIG. 6. shows the results.

FIG. 6 reveals that the boehmite of the invention can adsorb phosphate ions at a higher rate than the dried aluminum hydroxide gel.

EXAMPLE 2

A 700 ml quantity of water was added to 500 g of an aluminum hydroxide gel slurry (12.36% $Al_2O_3$). The mixture was heated to 80° C. with stirring and heat-treated at the same temperature for 3 hours. After cooling, the mixture was dried with a spray drier, giving a powder of the boehmite of the invention. Table 2 below shows properties of the powder.

COMPARISON EXAMPLE 2

A 500 g quantity of aluminum hydroxide gel slurry (12.36% $Al_2O_3$) was placed into a 5l-vol. autoclave and 2.5 l of water was added. The mixture was heated to 120° C. with stirring and heat-treated at the same temperature for 6 hours. After cooling, the mixture was filtered with Buchner funnel, and the cake of the residue was dried at 70° C. The dried product was pulverized in a mortar and the powder was passed through a sieve (100 mesh), giving a boehmite powder. Table 2 below shows properties of the powder.

TABLE 2

|  | Example 2 | Comparison Example 2 |
| --- | --- | --- |
| $Al_2O_3$ (%) | 64.85 | 67.34 |
| Decreased amount on drying (%) | 14.47 | 11.87 |
| Decreased amount on heating (%) | 35.15 | 32.66 |
| Value of n in the formula: $AlO(OH) \cdot nH_2O$ | 0.40 | 0.37 |
| Specific surface area (m²/g) | 225.7 | 170.6 |
| Amount of active OH group (meq/g) | 0.390 | 0.150 |
| Percentage of adsorption of phosphate ions (%) | 83.9 | 26.9 |
| Crystaline structure (obtained by X-ray diffraction) | Boehmite | Boehmite |

EXPERIMENT EXAMPLE 3

Figure 7:
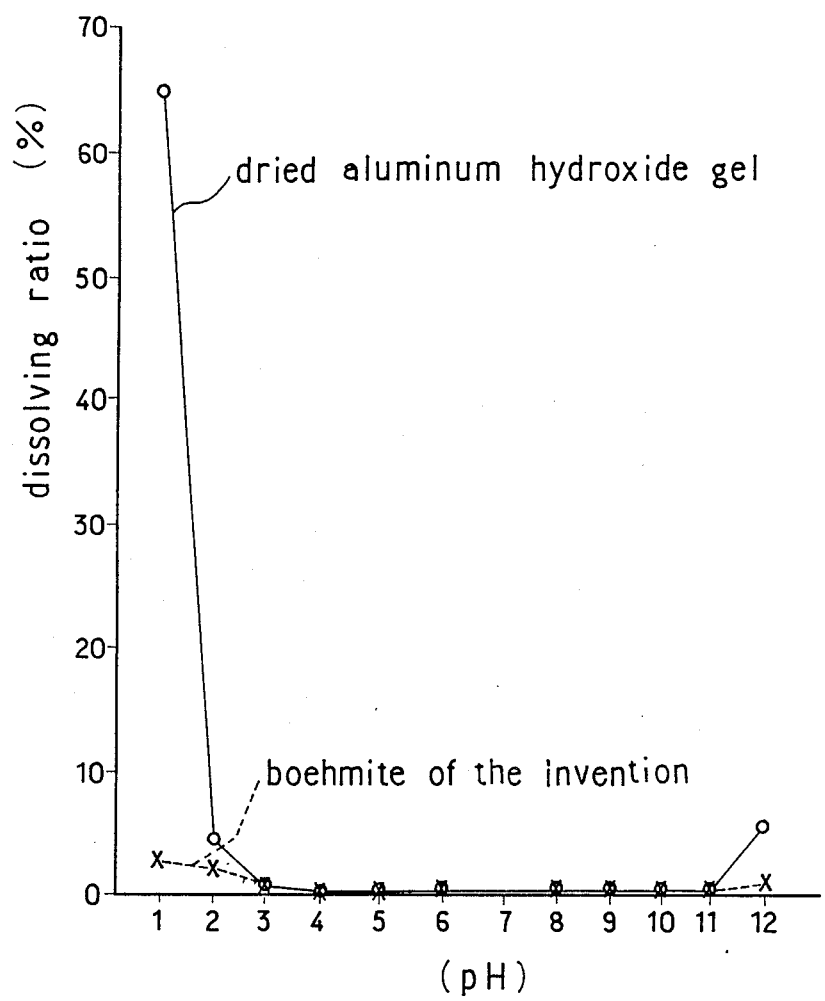

The boehmite of the invention obtained in Example 2 and dried aluminum hydroxide gel (Japanese Pharmacopeia) were tested for acid resistance and alkali resistance by the following method. A 100 ml quantity of artificial body fluid having its pH adjusted to each level was placed into a conical flask with a ground stopper and 1 g of specimen was placed. The mixture was stirred at 37° C. for 1 hour. After stirring, the mixture was filtered with a filter paper No. 6. The $Al_2O_3$ content in the filtrate was measured and the dissolving ratio (dissolved $Al_2O_3$/total $Al_2O_3$) was obtained. FIG. 7 shows the results.

FIG. 7 reveals that the boehmite of the invention, when mixed with a fluid with a strongly alkaline to strongly acidic level, was found to have dissolved out little or no Al ion.

We claim:
1. An orally administrable phosphate ion-absorbing composition comprising an effective phosphate ion-adsorbing amount of a beohmite-type aluminum hydroxide which is presented by the formula

$$AlO(OH) \cdot nH_2O$$

wherein $0 \leq n < 1$, said aluminum hydroxide containing on the surface thereof about 0.2 to about 1.0 meq of active OH group per gram thereof and having a BET specific surface area of at least about 200 m² per gram thereof.

2. The orally administrable phosphate ion-adsorbing composition according to claim 1 wherein $0.3 \leq n \leq 0.6$.

3. The orally administrable phosphate ion-adsorbing composition according to claim 1 wherein the aluminum hydroxide contains on the surface thereof about 0.3 to about 0.9 meq of active OH group per gram thereof.

4. The orally administrable phosphate ion-adsorbing composition according to claim 1 wherein the aluminum hydroxide has a BET specific surface area of about 200 to about 400 m² per gram thereof.

5. A phosphate ion adsorbing method comprising orally administering to a patient in need thereof, at a daily dose of about 3 to about 6 g per adult, an orally administrable phosphate ion-adsorbing composition comprising an effective phosphate ion-adsorbing amount of a boehmite-type aluminum hydroxide which is represented by the formula $$AlO(OH) \cdot nH_2O$$

wherein $0 \leq n < 1$, said aluminum hydroxide containing on the surface thereof about 0.2 to about 1.0 meq of active OH group per gram thereof and having a DET specific surface area of at least about 200 m² per gram thereof.

6. The method according to claim 5 wherein $0 \leq n \leq 0.6$.

7. The method according to claim 5 wherein the aluminum hydroxide contains on the surface thereof about 0.3 to about 0.9 meq of active OH group per gram thereof.

8. The method according to claim 5 wherein the aluminum hydroxide has a BET specific surface area of about 200 to about 400 m² per gram thereof.

* * * * *